| United States Patent [19] | [11] Patent Number: 5,053,559 |
| Jefford | [45] Date of Patent: Oct. 1, 1991 |

[54] CLEAVAGE OF 1,2,4-TRIOXANES

[75] Inventor: Charles W. Jefford, Troinex, Switzerland

[73] Assignee: Oxaco S.A., Geneve, Switzerland

[21] Appl. No.: 458,786

[22] Filed: Dec. 29, 1989

[51] Int. Cl.$^5$ .................... C07C 29/14; C07C 27/04
[52] U.S. Cl. .................. 568/814; 568/426; 568/485; 568/844
[58] Field of Search ............ 568/426, 485, 486, 814, 568/865, 844, 484

[56] References Cited

U.S. PATENT DOCUMENTS 4,386,219  5/1983  Merger et al. ................ 568/814
4,482,760  11/1984  Kleemann et al. ............. 568/814

FOREIGN PATENT DOCUMENTS 135933   12/1974  Japan ............................ 568/814
1009083  11/1965  United Kingdom ......... 568/814

*Primary Examiner*—Werren B. Lone
*Attorney, Agent, or Firm*—L. Dan Tucker

[57] ABSTRACT

1,2,4-Trioxanes are subjected to reductive cleavage, thereby to produce a 1,2-diol and carbonyl compound. The process has applications both in the synthesis of 1,2-diols and the protection, in the course of organic synthesis, of carbonyl compounds.

10 Claims, No Drawings

CLEAVAGE OF 1,2,4-TRIOXANES

The invention is concerned with a process for the cleavage of 1,2,4-trioxanes and to the use of such a process in organic chemical synthesis, particularly in the synthesis of 1,2-diols and/or the protection of carboxyl groups.

1,2,4-Trioxanes are compounds containing the skeletal structure:

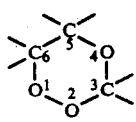

(A)

Methods have been recently developed for preparing a wide range of monocyclic and bicyclic 1,2,4-trioxanes (C. W. Jefford, D. Jaggi, J. Boukouvalas, and S. Hohmoto. *J. Am. Chem. Soc.*, 1983, 105. 6497; C. W. Jefford, J. Boukouvales, and S. Kohmoto. *Helv. Chim. Acta.* 1983, 66, 2615; C. W. Jefford, S. Kohomoto, J. Boukouvalas and U. Burger, *J. Am. Chem. Soc.*, 1983, 105. 6498; C. W. Jefford, D. Jaggi, J. Boukouvalas, S. Kohmoto, and G. Bernardinelli, *Helv. Chim. Acta.*, 1964, 67, 1104; C. W. Jefford, J. Boukouvales, and S. Kohmoto, *J. Chem. Soc., Chem. Commun.*, 1984, 523; C. W. Jefford, D. Jaggi, S. Hohmoto, J. Boukouvalas, and G. Bernardinelli, *Helv. Chim. Acta.* 1984, 67, 2254). The 1,2,4-trioxanes thus produced have been used as starting materials for the preparation of α-keto acids (C. W. Jefford, J.-C. Rossier, and J. Boukouvalas, *J. Chem. Soc., Chem. Commun.*, 1986, 1701), 1,2-diol monoesters (C. W. Jefford, S. Kohmoto, J.-C. Rossier, and J. Boukouvales, *J. Chem. Soc., Chem. Commun.*, 1985, 1983) and 1,2-diols (C. W. Jefford, J.-C. Rossier, and J. Boukouvalas. *J. Chem. Soc., Chem. Commun.*, 1987, 1593). A typical case is the treatment fo the cis-fused derivative of formula (1) below with benzylamine for several days. Aminolysis occurs to give a cis-1,2- diol and N-benzylformamide. A limiting condition for this mild process is that the C3 position must be unsubstituted.

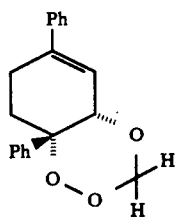

We have now found, in accordance with the present invention, that 1,2,4-trioxanes, regardless of the degree of C3 substitution, can be induced to cleanly liberate the C5, C6 1,2-diol together with the corresponding C3 carbonyl derivative by reductive cleavage, for example with zinc and acetic acid.

Basically, therefore, the present invention provides a process for the simultaneous production of a diol and a carbonyl compound which process comprises subjecting a 1,2,4-trioxane to reductive cleavage, thereby to produce a 1,2-diol (at the C5 and C6 carbon atoms of the original trioxane, as shown below) and a carbonyl compound (at the C3 carbon atom of the original trioxane, as shown below).

The process of the invention may be schematically illustrated as follows:

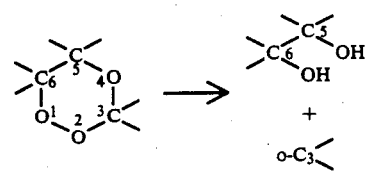

Since the trioxane will generally be prepared from the carbonyl compound (which gives the C3 carbon atom in the eventual trioxane ring), the process in accordance with the invention serves as a step in a useful method of protecting a carbonly group during the course of organic synthesis. However, the diol generated by the process of the invention is different from the starting materials used in the preparation of the trioxane and the process of the invention thus also serves as a route for the preparation of 1,2-diols.

Whatever the intended purpose, however, the basic process of the invention comprises the reductive cleavage of the trioxane.

The procedure is both simple and short. Treatment of the trioxane, neat or in ether solution, for example with an excess of zinc powder and glacial acetic acid, followed by filtration, e.g. through celite, gives the desired diol and carbonyl compound (and solvent where used). If the carbonyl compound is volatile (as is desirable when the aim of the process is to obtain a diol) then evaporation of the carbonyl compound and solvent (if any) gives the desired diol essentially free of impurities. Other effective reducing systems can be used in place of zinc with acetic acid and suitable systems include sodium borohydride and dissolving metals, such as lithium, sodium and potassium, in solvents such as liquid ammonia and various alcohols. The progress of the reduction can be conveniently monitored by tlc in order to ensure that all the trioxane is consumed.

Suitable trioxanes for use as starting materials in the process of the invention may be generally represented by the formula:

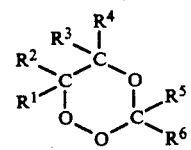

(I)

in which $R^1$, $R^2$ and $R^3$ are the same or are different and each is acyclic or cyclic hydrocarbyl group optionally interrupted by one or more heteroatoma such as oxygen, sulphur or nitrogen, and optionally substituted with one or more non-interfering substituents such as other hydrocarbyl groups, halogen atoms, nitro groups etc., or $R^2$ together with $R^1$ or $R^3$ and the adjacent carbon atom(s) forms a carocyclic or heterocyclic ring system optionally fused to one or more other ring systems and or optionally substituted with one or more non-interfering substituents as discussed above; $R^4$ is a hydrogen atom or an acyclic or cyclic hydrocarbyl group optionally interrupted or substituted as discussed for the groups $R^1$, $R^2$ and $R^3$; and $R^5$ and $R^6$ are the same or are different and each is a hydrogen atom or an acyclic or cyclic hydrocarbyl group otpionally interrupted by one ore more heteroatoms, such as oxygen, sulphur or nitrogen, and/or optionally substituted by one or more non-interfering substituents (as discussed above for the $R^1$, $R^2$ and $R^3$); or $R^5$ and $R^6$, together with the adjacent carbon atom, form a carbocyclic or heterocyclic ring system optionallyl fused with one or more other ring systems and/or optionally substituted with one or more non-interfering substituents as discussed above.

The starting trioxanes are conveniently prepared by reaction of a carbonyl compound with a 1,4-endoperoxide or a 1,2-dioxetane, suitably in the presence of trimethylsilyl trifluoromethanesulphonate (TMSOTf) as discussed in *J. Chem. Soc., Chem Commun.* 1984, at pages 523 and 524.

Thus, the trioxane may be prepared from a carbonyl compound of the formula $R^5R^6CO$ (in which $R^5$ and $R^6$ are as defined above) and a 1,4-endoperoxide of the formula:

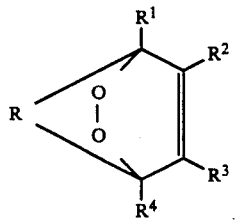

(II)

(in which the group $R^1$, $R^2$, $R^3$ and $R^4$ are as defined above and the group R represents a substituted or unsubstituted methylene or ethylene group) to give a trioxane of formula (I).

Alternatively the trioxane may be prepared by reacting the carbonyl compound of the formula $R^4R^5CO$ with a 1,2-dioxetane of the formula:

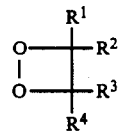

(III)

(in which $R^1$, $R^2$, $R^3$ and $R^4$ have the meanings defined above and, preferably, $R^1$ and $R^2$ together with the adjacent carbon atom form a substituted or unsubstituted cyclic group) to give a compound of formula (I) above.

Accordingly, using the process of the invention it is possible to convert 1,4,-endoperoxide of formula III above to a diol of the formula:

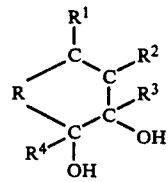

(IV)

or to convert a 1,2-dioxetane of formula III above to a diol of the formula:

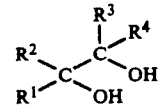

(V)

When, as discussed above the principal end use of the process of the invention is to provide a 1,2 diol, then the carbonyl compound employed to make the trioxane is preferably a volatile compound such as formaldehyde, acetaldehyde or acetone.

Alternatively, as mentioned above, the process of the invention may be used as a process for the protection of a carbonyl group. In this case the carbonyl compound to be protected is suitably reacted with a 1,4-endoperoxide of formula II above, e.g. 1,4-diphenyl-1,4-epidioxy-cyclopent-2-ene; 1,4-diphenyl-1,4-epidioxy-1,2,3,4-tetrahydrobenzene; or 1,4-dimethyl-1,4-epidioxy-1,4-dihydronaphthalene.

It may noted that, interestingly, the trioxane ring, in contrast, for example, to an acotal system used as a protective group for carbonyl groups, is resistant to acid hydrolysis.

In order that the invention may be well understood the following Examples are given by way of illustration only.

EXAMPLES 1-4

These examples are intended to particularly illustrate the use of the process in accordance with the invention as a process for the protection of 1,2-diois.

The starting compounds used in these examples were all prepared following the procedure described in *J. Chem. Soc., Chem. Commun.* 1984, 523/4.

In Example 1, the starting compound of the formula:

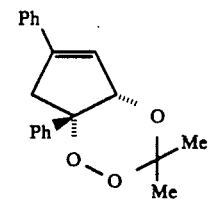

was subjected to reductive cleavage with zinc/acetic acid at 16° C. for 20 minutes to give acetone and, in 98% yield, the diol of the formula:

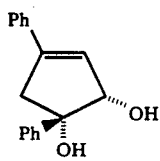

In Examples 2-4, starting material of the formula:

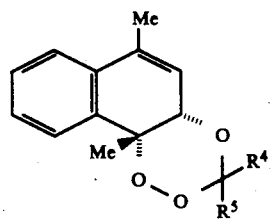

(in which R⁴ and R⁵ have the meanings given in Table 1 below) were each subjected to reductive cleavage with zinc/acetic acid, for the time and at the temperature given in Table 1, to give a carbonyl compound R⁴R⁵CO and, in the yield noted in Table 1, a diol of the formula:

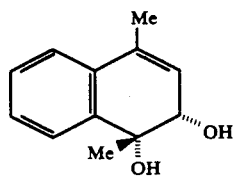

TABLE 1

| Example | R⁴ | R⁵ | Time (min) | Time (°C.) | Yield (%) |
|---|---|---|---|---|---|
| 2 | Me | Me | 20 | 18 | 100 |
| 3 | H | Me | 90 | −5 | 94 |
| 4 | H | H | 15 | 16 | 99 |

EXAMPLES 5 AND 6

These Examples are intended to more particularly illustrate the use of the process of the invention in the protection of carbonyl groups.

In each Example a cyclodexadioine mono-acetal of the formula:

(in which X is as defined in Table 2 below) was treated with a two-fold molar excess of 1,4-dimethyl-1,4-epidioxy-1,4-dihydronaphthalene in the presence of trimenthylsilyl trifluoromethanesulphonate (TMSOTf, 0.16 mol. equiv.) and 2,6-di-t-butylpyridine (DTBP, 0.7 mol. equiv.) in dichloromethane at −78° C. to give, in virtually quantitative yield, a trioxane of the formula:

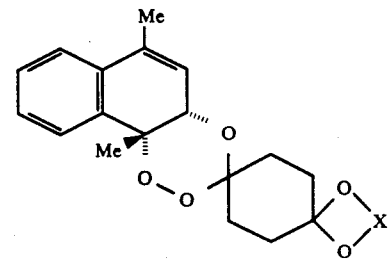

The trioxanes were each subjected to reductive cleavage with zinc/acetic acid, for the time and at the temperature given in Table 2, to give, in the yield noted, the starting ketone and the diol obtained in Example 2.

TABLE 2

| Example | X | Time (min) | Temp. (°C.) | Yield (%) |
|---|---|---|---|---|
| 5 | —(CH₂)₂— | 20 | 16 | 77 |
| 6 | —CH₂—C(Me)₂CH₂— | 90 | −17 | 98 |

Acid hydrolysis of the trioxane of Example 5 using 1M sulphuric acid in tetrahydrofuran for 16 hours at 20° C. gave, in 85% yield, the compound of the formula:

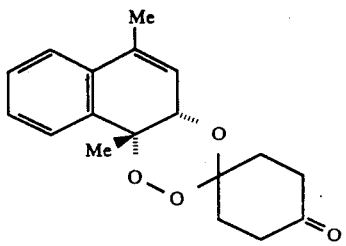

A further example of the preparation of 1,2-diol by the process of the invention is provided by the synthesis of a constituent of the essential oil of Ferula jaeschkeanna of the formula:

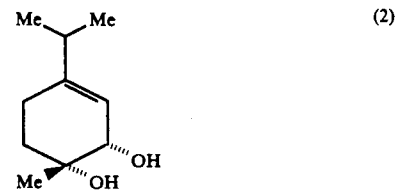

(2)

2

The first step comprises opening the peroxide ring in ascaridole by reaction with trimethylsilyl triflorome- thane sulphonate with cyclopentanone so forming the dimethyltrioxane derivative, in accordance with the scheme:

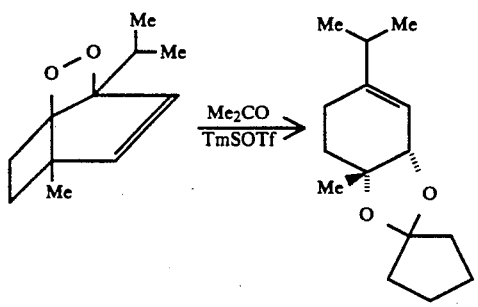

reductive cleavage using zinc/acetatic acid to give the desired diol of formula (2) and acetone.

A further example of protection of a carbonyl function by method of the invention is provided by the synthesis of the compound:

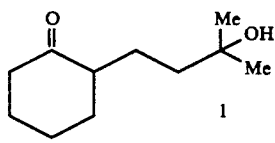

In the first step, an alkylated cyclohexanone is prepared in accordance with the scheme:

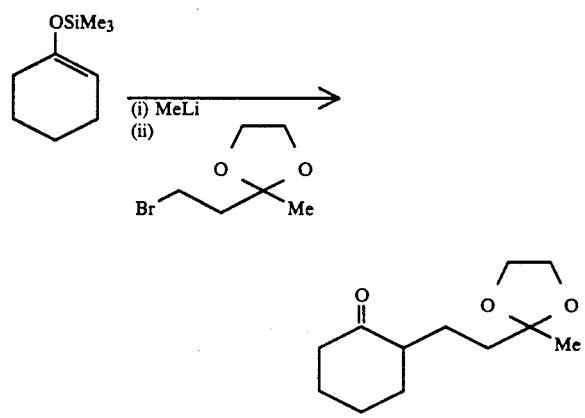

The carbonyl group of the cyclohexanone is then protected by reaction with 1,4-dimethyl-1,4-epidoxy-1,4-dihydronaphtalene in the presence of TMSOTf and trimethylsilyl di-t-butyl pyridine to give a protected compound which is then subjected to acid hydrolysis to liberate only the acetalized keto group in accordance with the scheme:

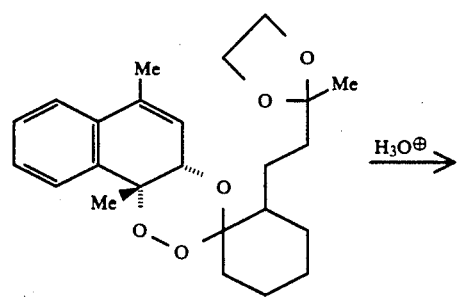

-continued

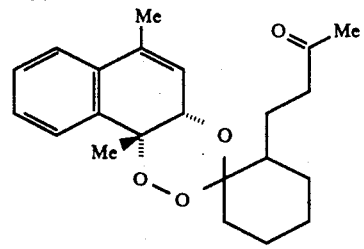

The free ketone group is then reacted with methyl magnesium bromide and the resultant compound is then subjected to reductive cleavage with zinc/acetic acid to give a diol and the desired compound in accordance with the scheme:

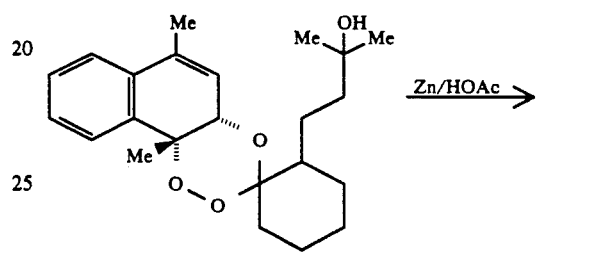

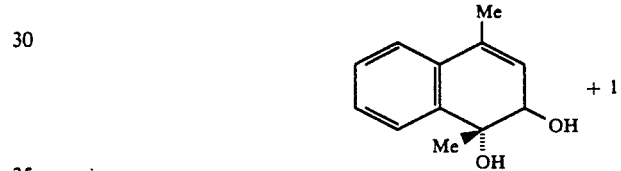

I claim:
1. A process for reductive cleavage of 1,2,4-trioxanes for simultaneous preparation of 1,2-diol and carbonyl compound, the 1,2,4-trioxanes represented by formula (1); the 1,2 diols represented by formula (2); and the carbonyl compounds represented by formula (3):

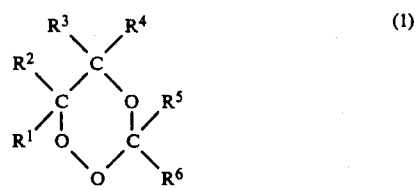

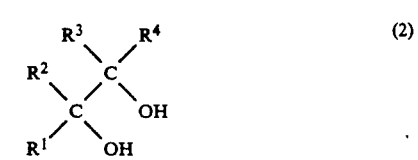

wherein $R^1$, $R^2$, $R^3$, $R^4$, $R^5$ and $R^6$ are the same or different and are hydrogen, acyclic or cyclic hydrocarbyl groups;

the reductive cleavage process in the presence of an organic acid, a metal or metal compound selected from the group consisting of sodium, lithium, potassium and sodium borohydride; at a temperature of from about −10° C. to ambient temperature.

2. A process as claimed in claim 1 in which the reductive cleavage is effected using a zinc/acetic acid system.

3. A process as claimed in claim 1 in which the 1,2,4-trioxane is one obtained by reacting a carbonyl compound with a 1,4-endoperoxide or 1,2-oxetane compound.

4. A process according to claim 1 wherein the organic acid is acetic acid.

5. A process according to claim 1 wherein $R^2$ together with $R^1$ or $R^3$ and the adjacent carbon atom(s) form a carbocyclic ring or $R^5$ and $R^6$ together with adjacent carbon atom(s) form a carbocyclic ring.

6. A process according to claim 1 wherein $R^1$, $R^2$, $R^3$, $R^4$, $R^5$ and $R^6$ are substituted with one or more non-interfering substituents selected from the group consisting of oxygen, sulphur, nitrogen, hydrocarbyl groups, halogen atoms and nitro groups.

7. A process according to claim 1 wherein $R^5$ and $R^6$ are comprised of at least one carbon atom.

8. A process according to claim 1 wherein $R^1$, $R^2$, $R^3$, $R^4$, $R^5$ and $R^6$ are comprised of from 1 to about 20 carbon atoms.

9. A process according to claim 1 wherein the process is applied to the synthesis and separation of the 1,2-diols from the carbonyl compounds.

10. A process according to claim 1 wherein the process is applied to the protection of the carbonyl compounds in the course of organic synthesis of 1,2 diols.

* * * * *